United States Patent
Bacharach et al.

(10) Patent No.: US 10,537,631 B2
(45) Date of Patent: *Jan. 21, 2020

(54) TILAPIA LAKE VIRUS VACCINES

(71) Applicants: The State of Israel, Ministry of Agriculture & Rural Development, Kimron Veterinary Institute, Beit-Dagan (IL); Ramot At Tel-Aviv University Ltd., Tel-Aviv (IL)

(72) Inventors: Eran Bacharach, Tel-Aviv (IL); Avi Eldar, Ramat Hasharon (IL)

(73) Assignees: The State of Israel, Ministry of Agriculture & Rural Developement, Kimron Veterinary Institute, Beit-Dagan (IL); Ramot At Tel-Aviv University Ltd., Tel-Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/102,037

(22) Filed: Aug. 13, 2018

(65) Prior Publication Data

US 2019/0216914 A1 Jul. 18, 2019

Related U.S. Application Data

(63) Continuation of application No. 15/645,718, filed on Jul. 10, 2017, now Pat. No. 10,071,152, which is a continuation of application No. 15/117,833, filed as application No. PCT/IL2015/050158 on Feb. 11, 2015, now Pat. No. 9,730,998.

(30) Foreign Application Priority Data

Feb. 13, 2014 (IL) .......................... 230970

(51) Int. Cl.
*A61K 39/12* (2006.01)
*A61P 31/14* (2006.01)
*A61K 9/00* (2006.01)
*C12N 7/00* (2006.01)
*A61K 39/00* (2006.01)

(52) U.S. Cl.
CPC ............ *A61K 39/12* (2013.01); *A61K 9/0014* (2013.01); *A61K 9/0019* (2013.01); *A61K 9/0056* (2013.01); *A61P 31/14* (2018.01); *C12N 7/00* (2013.01); *A61K 2039/5254* (2013.01); *A61K 2039/552* (2013.01); *C12N 2760/00* (2013.01); *C12N 2760/00011* (2013.01); *C12N 2760/00021* (2013.01); *C12N 2760/00022* (2013.01); *C12N 2760/00034* (2013.01)

(58) Field of Classification Search
CPC ............... A61K 39/12; A61K 2039/53; A61K 2039/525; C12N 7/00; C12N 15/86; C12N 2310/11; C12N 15/01; C12N 2760/00043; C12N 2760/00051; C12N 2760/00021; C12N 2760/00022; C12N 2760/00034; C07K 14/005
See application file for complete search history.

(56) References Cited

FOREIGN PATENT DOCUMENTS

| CN | 101068566 A | 11/2007 |
|---|---|---|
| CN | 101890159 A | 11/2010 |
| CN | 102847146 A | 1/2013 |
| RU | 2492557 C1 | 9/2013 |

OTHER PUBLICATIONS

First Office Action, Chinese Patent Application No. 201580008562. 3, dated Mar. 28, 2019, 12 pages.

*Primary Examiner* — Rachel B Gill
(74) *Attorney, Agent, or Firm* — Fenwick & West LLP

(57) ABSTRACT

The present invention relates to vaccine compositions comprising attenuated strain of Tilapia Lake Virus (TiLV) for protecting tilapia fish against infection by (TiLV). The invention also relates to methods for using the vaccines to protect tilapines from TiLV-induced disease.

19 Claims, No Drawings
Specification includes a Sequence Listing.

TILAPIA LAKE VIRUS VACCINES

RELATED APPLICATIONS

This application is a continuation of U.S. application Ser. No. 15/645,718, which is a continuation of U.S. application Ser. No. 15/117,833, which is a 35 U.S.C. 371 national stage filing of International Application No. PCT/IL2015/050158, filed on Feb. 11, 2015, which claims priority from Israel Patent Application No. 230970 filed on Feb. 13, 2014. The contents of the aforementioned applications are hereby incorporated by reference.

SEQUENCE LISTING

This application contains a Sequence Listing which has been filed electronically in ASCII format and is hereby incorporated by reference in its entirety. Said ASCII copy created on Sep. 21, 2017, is named "SL_31223_ST25.txt" and is 2 kilobytes in size.

FIELD OF THE INVENTION

This invention relates to vaccines for the protection of fish from viral diseases. In particular, the present invention relates to vaccine compositions for the prevention of Tilapia Lake Virus (TiLV)-induced disease in fish, particularly tilapines. This invention also relates to methods for using the vaccines to protect tilapines from TiLV-induced disease.

BACKGROUND OF THE INVENTION

During the last years, catch fish quantities in the Sea of Galilee (Kinneret Lake) in Israel have been subjected to a persistent decline. Interestingly, although the lake hosts some 27 species of fish (19 of which are endemic), encompassing members of the families: ciclidae, cyprinidae, mugillidae and claridae, catch cutback of tilapines were particularly striking. For the main edible fish of the lake, *Sarthoredon galilaeus*, annual yields decreased from 316 tons in 2005, to 51, 20 and 45 tons in 2007, 2009 and 2010, respectively. Being a grazing fish, *S. galilaeus* contributes to maintain the ecological balance between unicellular populations. Hence, above and beyond any economical impact, the significant decline of St. Peter's fish populations, as well as those of the other lake tilapines, such as *Tilapia zilli* (common tilapia), *Oreochromis aureus* (Jordan tilapia), *Astatotilapia flaviijosephi*, and *Tristamella simmoni slintermedia*, represents a definite threat to the entire ecosystem. The reasons for the decline were not clear.

Similarly, starting from the summer of 2009, episodes of massive losses of tilapia were recorded in fish farms all over Israel. These outbreaks were distinguished by waves of mortalities, spreading centripetally from one pond to the other. Interestingly, fish morbidity and mortality remained restricted to tilapines (*Sarthoredon* and *Oreochromis* spp. and hybrids). Several species reared in community with tilapines, such as carps (*Cyprinus carpio*), Grey mullets (*Mugil cephalus*) and others were found to be completely asymptomatic, even after long-term cohabitation. Moreover, once the initial wave of mortality has ceased, no more outbreaks were recorded in the same pond. As in the case of the lake, no apparent reason for the mortalities was identified. Routine monitoring of toxins did not reveal any abnormalities and no major ecological variations were recorded; meticulous detection of pathogens did not contribute to resolve the enigma.

However, heightened surveillance has led to the recognition of a phenomenon where—both in open waters and in farm ponds, well-nourished but weakened fish are perceived by black discoloration, skin abrasions and ocular degenerations. Histological analysis of diseased fish revealed the presence of augmented melano-macrophage centers (MMCs), which indicates an on-going pathological course.

The inventors have identified and isolated the causal agent of the tilapines disease, which is a novel, yet unidentified, RNA virus. The virus, hereinafter referred to as Tilapia Lake Virus (TiLV) was detected in 25 suspected outbreaks, collected from cultured tilapia in various parts of Israel, as well as from wild fish in the Sea of Galilee.

Vaccination against viral infection by bath immersion immunization offers several advantages over other routes of immunization. Among these advantages are lower cost per fish immunized, mass immunization of large numbers of fish, reduced stress, significantly higher rates of fish survival and the absence of adverse reactions to vaccination. Furthermore, bath immersion vaccination is an effective method for mass vaccination of smaller fish that cannot be injected. Alternatively, IP injection of commercially available fish vaccines is commonly employed on fresh or marine aquaculture farms due to their reliability and high efficacy despite high cost per fish immunized and stress to the fish.

Contrary to human vaccines, veterinary products (i.e. fish vaccines) have to be, primarily, cost-effective. Attenuated live vaccines are considered as "low-cost" biologicals which can be produced at relatively simple facilities and do not require the use of expensive products. Furthermore, as attenuated vaccines mimic natural infection, and a strong cellular and humoral immunity is induced after immunization, they are an excellent choice for fish medicine.

Commercial vaccines are available for a wide variety of viral and bacterial diseases. These include killed, attenuated and sub-unit vaccines.

It is therefore an object of the present invention to provide live-attenuated TiLV strains which can be used for the preparation of a vaccine.

It is another object of the invention to provide a method for the preparation of vaccine compositions for the immunization of tilapines against TiLV.

SUMMARY OF THE INVENTION

In a first aspect, the present application provides a vaccine composition for protecting tilapia fish against infection by Tilapia Lake Virus (TiLV) comprising an attenuated strain of TiLV.

In some embodiments, the attenuated strain is obtained by sequential passages in tissue culture.

In some other embodiments, the attenuated strain is obtained by passages in a host.

In a specific embodiment, the attenuated strain is obtained by at least 12 sequential passages in tissue culture. In another specific embodiment, the attenuated strain is obtained by at least 17 sequential passages in tissue culture. In a further specific embodiment, the attenuated strain is obtained by at least 20 sequential passages in tissue culture.

In some further embodiments, the vaccine composition of the invention further comprises an acceptable carrier, diluent or adjuvant.

In another embodiment of the invention, the tilapia fish is a member of the Cichlidae family. In a specific embodiment, the tilapia fish is selected from the species *Sarotherodon*, *Tilapia*, and *Oreochromis*, or any hybrid thereof.

In a further aspect, the invention provides an isolated TiLV deposited at the Collection Nationale de Cultures de Microorganismes (CNCM) of Institut Pasteur (France), under the depository accession number CNCM I-4817.

In still a further aspect, the invention provides a method for immunizing tilapine fish against infection TiLV infection comprising administrating to said fish a vaccine composition comprising an attenuated strain of TiLV in an amount sufficient to induce immunity to subsequent infection by TiLV.

In some embodiments of the method of the invention, the vaccine composition is administered to the fish orally via food. In a specific embodiment, the vaccine composition is coated by protective coating.

In some other embodiments of the method of the invention, the vaccine composition is administered to the fish by injection. In some further embodiments, the vaccine composition is administered to the fish by dissolving or immersing the vaccine composition in the body of water. In some further embodiments, the immunity is induced in the fish by cohabitation. In some further embodiments, the vaccine composition is administered to the fish by spraying the composition on fish which are temporarily removed from the body of water.

Any of the above embodiments of the method of the invention may further comprise the step of maintaining the immunized fish in temperature of 31° C. for 3-5 days, followed by transfer to 22° C. for at least 25 days.

In still a further aspect, the invention provides a vaccine composition for use in preventing or treating infection caused by TiLV, wherein said composition comprises an attenuated strain of TiLV.

All the above and other characteristics and advantages of the invention will be further understood through the following illustrative and non-limitative description of embodiments thereof, with reference to the appended drawings. In the drawings the same numerals are sometimes used to indicate the same elements in different drawings.

DETAILED DESCRIPTION OF THE INVENTION

The inventors have recently identified a small, previously un-described, RNA virus, which is the causative agent of a fatal disease affecting both wild tilapines at the Sea of Galilee and cultured tilapia in fish farms all over Israel. As the virus was initially found in wild tilapines at the Sea of Galilee, the name Tilapia lake virus (TiLV) was given. The linkage between the (i) newly isolated disease, the (ii) "mysterious" disease and the (iii) decline in fish population was attained by fulfilling Koch's postulates.

Final evidence that the isolated virus is indeed the cause of the disease was based on the following data. (i) The virus was successfully isolated from infected fish, but not from naive specimens. (ii) Inoculation of the virus that was propagated in cell culture into naïve fish induced a fatal disease. (iii) The cultivation of specimen extracts from experimentally-infected fish yielded the same virus, which was propagated once again cell cultures. (iv) Three cycles of this ping-pong technique were successfully applied. (v) Cohabitation of TiLV-infected fish with naïve fish also induced the disease ("natural" transmission). (vi) Specific viral RNA was identified in sick fish and in infected cell cultures, but not in naïve fish or uninfected cultures.

The following characteristics of this virus and its associated disease are noteworthy: (i) The newly emerging RNA virus is very contagious. (ii) It is transmitted through water. (iii) Infection outcome is largely dependent on environmental and ecological conditions. (iv) The culture of the virus is feasible under a vast range of temperatures. (v) Apparently, TiLV has a rather narrow host range, infecting only tilapines while other species which are reared with tilapines remain unaffected. (vi) The viral RNA fragment sequences analyzed so far do not bear significant similarities to any known viral genomes and, (vii) Acquired immunity is attained in fish surviving primary exposure.

TiLV was propagated in the established E-11 line, inducing a cytopathic effect at 5 to 10 days post infection. Electron microscopy revealed naked icosahedral particles of 55 to 70 nm. Screening of representative libraries has allowed the identification of a TiLV-specific sequence, enabling to design a PCR tool for diagnosis. PCR screening confirmed the same virus is present both in the Sea of Galilee and in fish farms all over Israel.

Three main methods are commonly used to infect fish in the laboratory: cohabitation, bath immersion, and injection challenge. Although cohabitation and bath immersion most closely mimic natural exposure, the rate of infectivity by these routes is seldom relatively low.

The role of TiLV in inducing a disease was demonstrated by experimental intra-peritoneal infection with viral cultures of plaque-purified low in-vitro passages, or by cohabitation with diseased fish, all resulting in a fatal disease with over 80% mortality.

Cohabitation trials demonstrated that the disease is contagious, and that under controlled conditions mortalities occur within few days post-infection, leading to the death of 80-100% of the fish. Fish surviving initial mortalities were immune to further infections, demonstrating the mounting of an adaptive immunity.

Parameters for obtaining a disease by injection and by inducing a more natural, non-injectable induced disease were identified. Particularly, healthy Specific Pathogen Free (SPF) tilapia (*Oreochromis nilotica*), were challenged both with extracts from sick fish and supernatants from infected cell cultures.

Both injection and cohabitation routes were tested with environmental conditions mimicking real natural conditions (i.e., temperature of 26-28° C.). The behavior of the infected fish was monitored over time prior to more detailed histological analysis. Organ samples, from naturally and experimentally infected fish were processed with standard techniques (formalin fixation, sectioning and staining) and analyzed by light microscopy.

Attenuated Strain Vaccines

Live attenuated vaccines use live organisms that have been weakened so that they are avirulent, meaning they are unable to cause disease. Attenuation can be achieved in several ways:

- Naturally occurring related organisms that are avirulent in fish, including host range restricted organisms or naturally occurring avirulent strains.
- Multiple rounds of growth of virulent organisms under conditions that weaken the organism such as in tissue culture or harsh physical conditions.
- Chemical mutagenesis.
- Genetic manipulation of the organism to reduce virulence.

It is generally accepted that attenuated strains may serve as efficient vaccine strains as they mimic natural infection: they elicit strong cellular and antibody responses and often confer long immunity with only one dose. Attenuated microorganisms were successfully used for immunizing fish against several diseases. Since juvenile fish are grown in fish farms in large masses, one of the simplest and most economic methods to protect them against viral diseases is immunization via water.

Attenuated viral strains are typically obtained by selection of avirulent strains directly collected from fish, or by the extensive sequential passages of virulent strains in tissue culture. Passages can be performed at optimal viral conditions (in terms of temperature, host, cell-lines, chemical composition of media etc.) or at suboptimal conditions (i.e., growth at increasingly suboptimal temperatures or host). In either case, this procedure is followed by a selection/characterization process aiming to identify viral mutants that are highly immunogenic but demonstrate reduced virulence. These mutants are defined as "naturally occurring non-virulent strains", in contrast to the attenuated strains which are the result of chemical mutagenesis (using mutagenic substances such as 5-fluorouracile or hydroxylamine) or the use of genetic manipulation (viral reassortant, reverse genetics, etc.).

The live-attenuated viral strains according to the invention may be prepared by any of the above methods. In one specific embodiment of the invention, the viral agent is obtained by sequential passages in tissue culture. In another embodiment of the invention, the viral agent is obtained by passages in a host.

The terms "virus" and, "viral strain" and "strain" refer, without limitations, to closely related strains of the specific isolate described herein, namely any strain, which shares similar genotype and/or phenotype characteristics with this isolated viral strain. This includes slightly modified forms or variants of the virus, which retain the same functional activities, namely, additions, deletions or alternations of amino acids or nucleotides.

The term "avirulant strain" as used herein refers, without limitations, to a virus which is absent of all disease-producing abilities. Such avirulent viruses are attenuated viruses which are used in all types of immunizations including active and passive immunizations. Natural avirulent counterparts whose ability to cause TiLV is diminished are also encompassed.

The term "host" as used herein refers to a fish, specifically a member of the Cichlidae family, which is susceptible to TiLV infection.

In order to determine the number of passages required to obtain an attenuated TiLV strain, the inventors tested several numbers of passages (12, 17 and 20).

Groups of 30 healthy Specific Pathogen Free (SPF) fish (10 gram each) were exposed to the different vaccine strains of the invention, through bathing or i.p. injections. These groups were challenged with disease inducing by wild-type strain through cohabitation with diseased fish, 30-45 days post-vaccination. Survival rates of the vaccinated fish were determined and the relative percent survival (RPS) was calculated as detailed in Example 2. The results obtained demonstrate the efficiency of vaccine strains P17 and P20, inducing significant immunization of the vaccinated fish. All experiments were carried out in triplicates with temperature conditions of 25-28° C., which is the temperature of the naturally occurring disease.

Viral diseases of fish are typically temperature dependent. For example, viral hemorrhagic septicemia (VHS) occurs at temperature below 12° C., while Koi herpesvirus (KHV) infection necessitates temperatures ranging between 20-28° C. Thus, fish can be infected at non-permissive temperatures and mount an immune response without clinical disease. This approach has been proved successful in preventing disease in several instance, including, viral hemorrhagic septicemia (VHSV), KHV and viral nervous necrosis (VNN).

In one embodiments of the invention, the tilapines are infected as hereinbefore described and maintained in temperature of 22 or 31° C. for 3-5 days, before being transferred to temperatures of 31 or 22° C., respectively.

Accordingly, in one aspect the present invention provides specific vaccines for the immunization of tilapia fish against a newly discovered virus, namely TiLV.

The term "vaccine" as used herein refers to a substance capable of producing an immune response against infection caused by TiLV. The vaccines may contain live or inactivated or dead (killed) viruses or combinations thereof.

The terms "immunization" or "immune response" as used herein refer to an immunity which can elicit humoral and/or cell mediated immune responses to viral infection, or interfere with the activity, spread, or growth of the virus. Fish immunized by the vaccine of the present invention may experience limited or no growth and spread of the infectious virus.

The invention further relates to a method for immunizing tilapine fish against the viral infection caused by TiLV, said method comprising administration to susceptible fish a vaccine composition comprising live-attenuated TiLV. The vaccine is administered in an amount sufficient to induce immunity to subsequent infection by TiLV.

The vaccines according to the invention demonstrate significant protection in the cohabitation challenge model (RPS values ranging between 55-62%). These results are very similar to commercially available vaccines, such as the Salmon Anemia Virus (SAV) vaccine, which induces an average RPS of 65%.

The efficacy of the vaccine compositions of the present invention was tested using a challenge model that closely resembles the natural modality of infection, cohabitation. The data generated highlight the industrial feasibility of immunizing tilapines against the TiLV-induced disease.

It should be noted that the vaccine compositions according to the present invention are suitable for any type of fish that is susceptible to TiLV, and specifically members of the family Cichlidae, commonly known as tilapiine cichlids. Examples for economically important tilapines include the group of species contained within the genera *Oreochromis, Sarotherodon* and *Tilapia*. The use of hybrids of 2-4 species of tilapia is also quite popular in certain countries, and accordingly, species are infinite, due to all possible hybrids. Thus, the any hybrid of any species of tilapia fish is suitable for immunization according to the present invention.

Vaccine is defined herein in its broad sense to refer to any type of biological agent in an administrable form capable of stimulating a protective immune response in fish inoculated with the vaccine.

Effective immunization or vaccination dose or dosage is defined herein as being the amount that will induce complete or partial immunity in a vaccinated fish against a subsequent challenge by a virulent strain. The Efficacious vaccine is defined herein as a vaccine that offers equal or greater than about 50% protection against TiLV infections.

Attenuation, or inactivation, is defined as the loss of virulence of a pathogen. The loss of virulence is gradual in case of attenuation. The availability of specific vaccines (either attenuated strains or killed preparations) is a mainstay for the sustainability of aquaculture in infected zones. Technically, vaccination according to the invention can be performed through oral administration (via food), through the waterborne route (i.e., dispersion of the vaccine in the water body or through previously vaccinated fish shedding the attenuated virus to non-vaccinated fish), injection (parenteral administration, including the intradermal, intramuscular and intra-cavity procedures) or the air-spraying method.

In one embodiment of the invention, the vaccination of large fish stocks with the killed virus or with the live-attenuated virus is achieved by oral administration through the feed. The vaccine may be incorporated within the food coated by protective coatings.

In another embodiment, vaccination may be performed by injection, either as individual administration, which is also feasible in large scale, and is performed either by (hand) vaccinating professionals or, preferably, with the aid of semi-automatic machines.

In a further embodiment of the invention, the vaccination of large quantities of fish is performed by simultaneous administration of the live-attenuated virus to the entire fish population present in a body of water by dissolving or immersing the virus or the vaccine composition in the body of water.

Another option for vaccinating large stocks of fish by the attenuated vaccine takes advantage of its possibility for (limited) replication in the final host. Accordingly, in a still further embodiment of the invention, the vaccine composition is administered to a limited number of subjects, in which the attenuated virus replicates, sheds and propagates to other fish which are reared in community with the vaccinated fish.

In an additional embodiment of the invention, massive vaccination of fish is accomplished by spraying the fish, which are temporarily removed from the water for a short period, with the vaccine.

Immunity according to invention can be induced in susceptible fish by cohabitation of TiLV-infected fish with naïve fish.

Fish immunization according to the invention can take place in any natural or non-natural environment such as ponds, lakes, aquariums, fish farms and fresh water habitats.

The vaccine compositions of the invention can be effectively administered any time after the fish attains immune-competence, which for tilapia is at about two to fourteen days post-hatch.

Immunity is considered as having been induced in a fish population as evidenced by a decrease in the number of infected fish or an increase in the number of surviving fish compared to that of an unvaccinated control group.

The viral agents or viral strains are prepared for administration to fish by formulation in an immunologically effective amount or dosage. The dose may further include pharmaceutically acceptable carriers, diluents and/or adjuvants know in the art, such as water, physiological saline, oil (emulsion), liposomes, coating or encapsulating agents.

The present invention further encompasses the use of the live-attenuated viral strains for the preparation of a vaccine composition for immunizing tilapia fish against the infection caused by TiLV. The composition comprises as an active ingredient, a live-attenuated virus.

In another aspect, the invention provides a vaccine composition for use in preventing or treating infection caused by TiLV, wherein said composition comprises an attenuated strain of TiLV.

In another aspect, the invention encompasses the use of an attenuated strain of TiLV in the preparation of a vaccine composition for immunizing tilapia fish against the infection caused by TiLV. The composition comprises, as an active ingredient, a live-attenuated virus.

The invention will now be described with reference to specific examples and materials.

EXAMPLES

Materials and Methods
Cell Cultures

Eight established fish cell lines were used: (1) the CHSE-214 line (ATCC CRL 1681) from chinook salmon *Oncorhynchus tshawytscha*; (2) the BF-2 line (ATCC CCL 91); derived from bluegill *Lepomis macrocturus*; (3) the BB line (ATCC CCL 59) from brown bullhead *Ictalurus nebulosus*; (4-5) EPC and KF-1 from common carp *Cyprinus carpio*; (6) the RTG-2 line (ATCC CCL 55) from rainbow trout *Salmo gairdneri*; (7) the FHM line (ATCC CCL 42) from fat head minnow *Pimephales promelas*; and (8) E-11 from striped snakehead *Ophicephalus striatus*.

The original tilapia cell line used for virus culture, termed Til 13, was prepared as previously described elsewhere (Stenglein et. al., 2012). Briefly, 50 g anesthetized fish were sacrificed by anesthetic overdose, and the brains were removed aseptically. Brains were then minced with scissors, manually homogenized and passed through a 100 μm mesh grinders; cells were then washed and seeded in 12.5-ml sealed flasks (Becton-Dickinson, San Francisco, USA) at 25° C. Initial culture medium contained 80% Leibovitz (L-15) medium (Gibco, USA), 10% inactivated fetal calf serum (Gibco, USA) and 10% inactivated tilapia serum; media was supplemented with L-glutamine (300 mg/l), HEPES (1%), penicillin (100 μg/ml), streptomycin (100 μg/ml), and amphotericin B (0.25 μg/ml). During the first 21 days of incubation, 50% of medium were changed every week. Thereafter, monolayers around each clump were trypsinized and transferred into new 25 ml flasks (Cellstar; Greiner bio-one, Germany) with conditioned medium (50% old medium plus 50% new medium). Cultures of primary cells were passaged every other week; after 35 passages the line was considered stable; at this point tilapia serum was omitted, conditioning was stopped, and cells were split every 2-3 weeks.

Viruses and Virus Culture

A total of 25 TiLV isolates were obtained from suspected outbreaks that occurred from May 2011 to March 2013 in six different farms in Israel, located in various parts of Israel (Upper Galillee, Jordan valley and the Mediterranean coast), as well as from various species of wild tilapines at the Sea of Galilee. Outbreaks of farmed fish were defined as a sudden and unexplained rise in mortalities (2% daily, or more) for at least three consecutive days. If two wards were affected in the same farm simultaneously, these were classified as a single outbreak. Therefore, each isolate represents a distinct clinical outbreak. Viruses from wild fish were isolated from commercial catch fish displaying ocular lesions; each of these isolate represents a different catch. In order to minimize contamination risks, the brains and viscera (kidneys, livers, spleens and hearts) of the suspected fish were removed aseptically and manually homogenized with 9 volumes of Hanks' balanced salt solution (HBSS), centrifuged at 3000×g for 10 min, and the supernatants were filtered through 0.22 μm membrane filter (Starsdet, Germany). Filtrates were stored at −80° C. until used.

Test for Sensitivity to Virus Infection

Monolayers, covering 85 to 95% of the 25 cm$^2$ flasks (Cellstar; Greiner bio-one, Germany) were washed twice with HBSS and then 500 μl of the virus filtrate was inoculated in the cell culture. After incubation at 25° C. for 1 h, the flask was washed with HBSS, supplemented with L-15 medium (2% FBS), and incubated at 25° C. CPE were observed daily for 21 days.

Titration of Virus

The original virus-containing culture supernatant (strain TiLV 4/2011 obtained from the brain of St. Peter's fish) was cultured in E-11 cells and diluted serially in 10-fold increments with HBSS; 50 μl from each dilution was inoculated onto E-11 monolayers in 96-well plates. Four wells were used for each diluted sample. Plates were incubated at 25° C. and observed daily for CPE. After 7 days, the 50% tissue culture infectious dose ($TCID_{50}$ $ml^{-1}$) was calculated by the method of Reed & Muench (1938). Absolute quantification of viruses was obtained by Real-time PCR (see below).

Titration of Viral Growth

Since growth of fish viruses is seldom considered to be temperature-dependent, reflecting the pathogen's capability to cause the disease at a restricted range of temperatures. This propensity varies according to the fish species and the virus. To determine the extent of growth at different temperatures, strain TiLV 4/2011 was inoculated at an MOI (multiplicity of infection) of 1.0 (assessed via Real-Time PCR absolute quantification) the E-11 monolayer cultures in a 24-well plate at 15, 20, 25 and 30° C. for 21 days. Infected cultures were collected by scraping, freeze-thawed, centrifuged (3000×g 10 min), and serially diluted in 10-fold increments with HBSS. $TCID_{50}$ counts were determined as described above. Absolute quantification of viruses was obtained by Real-time PCR (see below).

Purification of Virus from Culture Medium

Cultured E-11 cells were infected with strain TiLV 4/2011, originally isolated from diseased *S. galilaeus* (St. Peter's fish) collected from the Kinneret lake in June 2011. The medium harvested from TiLV-infected cells was cleared of cells and cell debris by centrifugation for 10 min at 3,000×g. To further concentrate virus particles and separate them from particles of lower density, the supernatant was layered onto 2 ml of 30% (wt/vol) sucrose-TE buffer cushion, and centrifuged for 2 h in an T865 rotor at 65,000 rpm (Sorvall Discovery 905E). For further purification, the pellet was re-suspended in TE buffer and layered onto a sucrose step gradient. Each layer of the gradient consisted of 3 ml of sucrose in TE with concentrations of 70, 60, 50, 40, 30, 20 and 10% [wt/vol (from bottom to top)]. Ultracentrifugation was done in a TST41.14 rotor for 2 h at 40,000 rpm (Sorvall Discovery 905E). Bands were visualized, aspirated from tubes, and re-pelleted by centrifugation for 2 h in a T865 rotor at 65,000 rpm (Sorvall Discovery 905E). Final pellet was re-suspended in 3 ml of PBS. An aliquot of 100 μl was taken for inoculation of E-11 cells and monitoring of cytopathic effects (CPEs). The pellets were frozen at −80° C. until further investigation.

Isolation of Nucleic Acids from Purified Virions

Nucleic acids (RNA and DNA) were extracted from purified virion pellets by using peqGOLD Trifast [(Peqlab, Germany), for RNA] or High Pure PCR Template Preparation Kit [(Roche, Germany), for DNA].

Quantitative Real Time PCR

The One-Step Real-Time PCR assay was designed as a single-tube PCR probe hydrolysis (TaqMan) assay for detection and quantification of TiLV in infected tissues or in cultured monolayers.

Specific oligonucleotide primers and the fluorogenic probe were designed to target a specific 250 bp fragment of the 450 bp fragment previously identified among the *E. coli* library transformants. A protocol identical to the one described above was used with forward ME1 primer GTTGGGCACAAGGCATCCTA (SEQ ID NO:1), ME2 reverse primer TATCACGTGCGTACTCGTTCAGT (SEQ ID NO:2) and the FAM probe AGGGAACGGCTATTG (SEQ ID NO:3) (all written in 5'-3' direction; Hylab, Israel).

Reagents (qScript XLT One-Step RT-qPCR ToughMix) were purchased from Quanta biosciences (ND, USA). PCR mixtures were run with the following thermal cycling parameters; reverse transcription at 50° C. for 10 min, enzyme inactivation at 95° C. for 1 min, 45 cycles at 95° C. for 10 sec (denaturation), annealing and extension at 60° C. for 30 sec. The PCR assay was followed by a melt curve step with a heating rate of 0.5° C.\sec (for 10 sec) and continuous fluorescence measurement. All PCR products were of the predicted molecular weight, indicating that specific amplifications have occurred. Positive and negative controls consisting of TiLV cDNA and a nontemplate reaction mixture were included with each PCR run.

Real Time PCR Data Analysis

To quantify the TiLV cDNA concentrations, standard curves were generated by analyzing PCR products designed to a 250 bp fragment to serial dilutions of the plasmid containing the TiLV 450 bp DNA. Absolute viral quantification was reported to the 250 bp TiLV fragment, through evaluating and analyzing the ΔCt variation (final amount of cDNA template=25 ng/well). Relative quantification (RQ) of virions per cell was obtained using the 2-ΔΔCt method, by normalizing TiLV concentration to that of β-actin mRNA (reverse and forward primers 5'-GGGTCAGAAAGACA-GCTACGTT-3' (SEQ ID NO:4) and 5'-CTCAGCTCGTT-GTAGAAGGTGT-3' (SEQ ID NO:5) (Hassanin et. al., 2009), and considering the adjusted expression in the control group as reference (RQ=1). Quantitation was performed in duplicate for sample, and all values are presented as means±standard errors of the means (SEM).

The expression of β-actin as well as that of EF-1 α remained constant along the various experiments ($p>0.05$), while that of the 18S rDNA was lower ($p<0.05$), thus indicating the suitability of the chosen β-actin as normalizing gene.

Data were analyzed by the Applied Biosystems StepOne™ software v2.0 and expressed as RQ. Descriptive statistics (mean±standard deviation of mean) was carried out to describe RQ in both in vivo and in vitro experiments.

Experimental Procedures

Experimental Reproduction of the Disease

The tilapine species *Oreochromis niloticus* (strain Chitrellada) was grown at a SPF facility (UV-treated pathogen-free environment) at a constant temperature of 28° C. Fish were fed at a daily regimen of 2% wt/wt; due to steady daily water changes, water parameters ($O2>5$ ppm; $NH_4+<1$ ppm; NaCl<1 ppt) were kept invariable.

All experimental infections were carried out with TiLV isolate 4/2011. Isolate 4/2011 is a field strain (passage 1) that was amplified by one passage to establish a high-titer seed-stock (passage 2) which was aliquoted and kept frozen at −80° C. Before use, the virus was thawed and cultured de-novo (passage 3).

Isolate viral strain 4/2011 was deposited with at the Collection Nationale de Cultures de Microorganismes (CNCM) of Institut Pasteur (France) under the accession number CNCM I-4817 on Nov. 8, 2013.

Example 1

Experimental Reproduction of the Disease

For the artificial reproduction of the disease, 2.6×105 TCID50 (50% tissue culture infective dose) were injected intra-peritoneally to each fish (each weighting 30-35 gr.). All experiments were carried out in triplicates of groups (30 fish per group). During experimentations, fish were kept in 200-liter aquariums that were divided in three compartments by water-permeable grids which allowed water (but not fish) circulation throughout the aquarium; control group was always kept in middle. Cohabitation trials were carried out under the same conditions, with the infecting fish being located in the middle. Fish surviving primary intra-peritoneal (IP) infection were pooled. Three weeks afterwards the fish were divided to two duplicates of groups (each of 20 fish) and infected once again by IP injection. Control groups were injected with uninfected E-11 cultures.

Definitive proof that the isolated virus is the cause of the disease was obtained by a series of 3 serial "culture and infect" experiments where cultures from brains of diseased fish were used for re-infection of naive fish.

This series of infections was completed by injecting fish with a single plaque-isolated virus.

In order to mimic farm conditions more faithfully and assess the role of virus propagation and passages in susceptible populations (fish kept in closed environments, as in intensive fish farming), a series of five successive infections were carried out as following: a group of (clinically ill) experimentally infected fish were placed in the first compartment of the aquarium, while a group of naïve fish was placed in the second compartment. Once the first group of naïve fish has contracted the disease (20% mortality), a new group of naïve fish was introduced (to the third compartment) and the original group was removed, allowing the introduction of a new group in its place. These "ping-pong" serial infections were carried out for a total of five times.

Health conditions of fish were carefully monitored throughout the growing and experiment periods: external signs and mortality rates were monitored twice daily, for a total of 21 days. Ethical issues, animal care, experimental handling and safety regulations conformed to guidelines established by the Subcommittee on Laboratory Animal Care at the Israeli Veterinary Services.

Example 2

Passage-Attenuated Live Vaccines

Three variants of live-attenuated strains were explored as potential vaccine candidates. All variants consisted of the TiLV isolate 4/2011 which was serially passaged in-vitro; passages were performed in 25 cm$^2$ flasks according to the methodology described hereinbefore, making use of the cell line, Til 13.

The differences between the vaccine types consisted in the number of passages: the first vaccine strain, termed P12, was passaged 12 times, the second strain, denoted P17, was passaged 17 times, while the third, termed P20, was passaged 20 times. The last passages (12, 17 and 20, according to the strain) were performed in in 175 cm$^2$ flasks. Flasks were then freeze-thawed and cell debris were removed by centrifugation (3000×g 10 min). Viruses localized in the supernatant were quantified by the 50% tissue culture infectious dose ($TCID_{50}$ ml$^{-1}$), calculated by the method of Reed & Muench (1938) as well as by Real-Time PCR. Each of the vaccines was PBS-diluted to contain (in 100 μl of final dose) $TCID_{50}$ of $1.3\times10^2$.

Safety studies, including determination of potential residual virulence and possible reversion to virulence were addressed by (i) injecting (in three groups of 100 fish, each) ten-fold doses (i.e. $TCID_{50}$ of $1.3\times10^3$) of P12, P17 and P20 virus variants, and (ii) injecting (in three groups of 100 fish, each) 5 back-passages of each variant (in 100 μl of final dose) TCID 50 of $1.3\times10^2$. Mortality and adverse reactions were monitored for 30 days. Mortality and side-effects (adhesions and melanization of the viscera) were recorded 6 and 12 weeks post vaccination (n=15 per group, per sampling) using a modified Speilberg scale (Midtlyng and Lillehaug, 1998).

The fish and the setting for infecting vaccinated fish were, essentially, identical to what previously described in Example 1 under "Experimental reproduction of the disease". Briefly, groups of SPF Chitrellada *Oreochromis niloticus* (30 fish per group, each weighting 30-35 gr), were injected with 100 μl of PBS containing P12, P17 or P20 TiLV viruses. For relieving manipulations, fish were sedated by Metacaine (M5222, PHARMAQ Ltd, UK). Vaccination was performed by manual intra-peritoneal injection of 100 μl doses. Thereafter, vaccinated fish were kept in first compartment of the aquarium (see aquarium description in Example 1), while naïve fish (identical number and size) were kept in the second compartment. Three weeks after vaccination, infecting fish were introduced to the third compartment. Infecting fish consisted of 30 naïve fish which were infected by 6 h cohabitation with diseased fish held in an aquarium where virulence was augmented by 4 passages of the wild type virus. Tanks were monitored daily for clinical signs of disease or mortalities. Control fish were injected 100 μl of non-diluted culture media deriving from non-infected Til-13 cultures. Recorded mortality data was used for calculating Relative Percentage Survival (RPS), as described by Amend (1981):

RPS=1·[(Mortality (%) in treated group)/(Mortality (%) in control group)]×100.

Results: Specific TiLV Protection by Vaccination

The P12 vaccine strain was determined to contain $TCID_{50}$ $ml^{-1}$ of $7.0\times10^7$, corresponding to $5.2\times10^7$ Real-Time PCR enumerated viral particles, while that of the P17 vaccine contained a $TCID_{50}$ $ml^{-1}$ of $1.2\times10^8$, corresponding to $8.0\times10^7$ Real-Time PCR enumerated viral particles. For the P20 vaccine stain, the $TCID_{50}$ $ml^{-1}$ consisted of $8.9\times10^7$, corresponding to $8.7\times10^7$ Real-Time PCR viral particles.

Specific mortalities induced by challenges with the wild-type strain began at days 2 to 4 and lasted for 5 to 7 days. All dead fish were TiLV positive. Pre-agonic signs included evident lethargy and slight melanosis. Apart from slight congestion, no other gross lesions were observed in the internal organs.

Survival rates and relative percentage survival (RPS) values of the different groups of vaccinated fish are shown in Table 1. In the fish vaccinated with P17, the RPS value was determined to be 58% (variations between the different groups=56-61%; P>0.05); the RPS of the P20 vaccinated fish—59% (ranges between groups=55-62%; P>0.05) was similar to that obtained with P17. The absolute survival rates of these groups were found to be 62 and 64%, respectively, while mortality rates in the control group and in the P11 vaccinated fish were 63%.

Safety data pointed out that, for P17 and P20 vaccine prototypes, neither five back-passages nor ten-fold increase of vaccine quantity gave rise to undesired effects (disease or mortalities).

TABLE 1

Relative Percentage Survival (RPS) (%) of challenged TiLV vaccinated Oreochromis niloticus by P12, P17 and P20 vaccines

| | Survival | Mortality (%) | RPS (%) |
|---|---|---|---|
| Control fish | 3 | 97 | — |
| P12 vaccinated fish | 37 | 63 | — |
| P17 vaccinated fish | 62 | 28 | 58 |
| P20 vaccinated fish | 64 | 26 | 56 |

The invention claimed is:

1. A vaccine composition comprising an attenuated strain of Tilapia Lake Virus (TiLV) obtained by selection of avirulent strain by serially passaging in vivo, for protecting tilapia fish against infection by virulent TiLV.

2. The vaccine composition according to claim 1, wherein the attenuated strain is obtained by passages in a host.

3. The vaccine composition according to claim 1, further comprising an acceptable adjuvant.

4. The vaccine composition according to claim 1, wherein the tilapia fish is a member of the Cichlidae family.

5. The vaccine composition according to claim 4, wherein the member of the Cichlidae family is selected from the species *Sarotherodon*, *Tilapia*, and *Oreochromis*, or any hybrid thereof.

6. The vaccine composition according to claim 1, wherein said TiLV to be serially passaged in vivo is the isolate deposited at the Collection Nationale de Cultures de Microorganismes (CNCM) of Institut Pasteur (France), under the depository accession number CNCM 1-4817.

7. A method for immunizing tilapia fish against TiLV infection comprising serially passaging in vivo Tilapia Lake Virus (TiLV) thereby obtaining an attenuated strain, and administering to said fish a vaccine composition comprising said attenuated strain of Tilapia Lake Virus (TiLV).

8. The method according to claim 7, wherein the attenuated strain is obtained by passages in a host.

9. The method according to claim 7, wherein the vaccine composition is administered to the fish orally via food.

10. The method of claim 9, wherein the vaccine composition is coated by protective coating.

11. The method according to claim 7, wherein the vaccine composition is administered to said fish by injection.

12. The method according to claim 7, wherein the vaccine composition is administered to said fish by dissolving or immersing the vaccine composition in the body of water.

13. The method according to claim 7, wherein the immunity is induced in said fish by cohabitation.

14. The method according to claim 7, further comprising maintaining the immunized fish in temperature of 31° C. for 3-5 days, followed by transfer to 22° C. for at least 25 days.

15. The method according to claim 7, wherein the attenuated strain is obtained by sequential passages in a host.

16. The method according to claim 7, wherein the vaccine composition further comprises an acceptable adjuvant.

17. The method according to claim 16, wherein the vaccine composition is administered to said fish by spraying the composition on fish which are temporarily removed from the body of water.

18. The method according to claim 7, wherein the tilapia fish is a member of the Cichlidae family.

19. The method according to claim 18, wherein the member of the Cichlidae family is selected from the species *Sarotherodon, Tilapia*, and *Oreochromis*, or hybrid thereof.

* * * * *

SEQUENCE LISTING

```
<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: PCR forward primer

<400> SEQUENCE: 1
gttgggcaca aggcatccta                                               20

<210> SEQ ID NO 2
<211> LENGTH: 23
<212> TYPE: DNA
<213> ORGANISM: Artificial Sequence
<220> FEATURE:
<223> OTHER INFORMATION: PCR reverse primer

<400> SEQUENCE: 2
tatcacgtgc gtactcgttc agt                                           23

<210> SEQ ID NO 3
<211> LENGTH: 15
<212> TYPE: DNA
<213> ORGANISM: Artificial Sequence
<220> FEATURE:
<223> OTHER INFORMATION: FAM probe

<400> SEQUENCE: 3
agggaacggc tattg                                                    15

<210> SEQ ID NO 4
<211> LENGTH: 22
<212> TYPE: DNA
<213> ORGANISM: Artificial Sequence
<220> FEATURE:
<223> OTHER INFORMATION: Reverse primer

<400> SEQUENCE: 4
gggtcagaaa gacagctacg tt                                            22

<210> SEQ ID NO 5
<211> LENGTH: 22
<212> TYPE: DNA
<213> ORGANISM: Artificial Sequence
<220> FEATURE:
<223> OTHER INFORMATION: Forward primer

<400> SEQUENCE: 5
ctcagctcgt tgtagaaggt gt                                            22
```